United States Patent [19]
Eek

[11] Patent Number: 5,908,847
[45] Date of Patent: Jun. 1, 1999

[54] COMBINATION OF A β-RECEPTOR BLOCKER AND AN OPIOID

[75] Inventor: Arne Eek, Trosa, Sweden

[73] Assignee: Astra AB, Sweden

[21] Appl. No.: 08/765,133

[22] PCT Filed: Oct. 3, 1996

[86] PCT No.: PCT/SE96/01248

§ 371 Date: Jan. 2, 1997

§ 102(e) Date: Jan. 2, 1997

[87] PCT Pub. No.: WO97/12634

PCT Pub. Date: Apr. 10, 1997

[30] Foreign Application Priority Data

Oct. 6, 1995 [SE] Sweden .................................. 9503476

[51] Int. Cl.$^6$ ........................ A61K 31/44; A61K 31/445; A61K 31/135
[52] U.S. Cl. .......................... 514/282; 514/326; 514/329; 514/652
[58] Field of Search ..................... 514/652, 282, 514/329, 326

[56] References Cited

U.S. PATENT DOCUMENTS 4,885,173 12/1989 Stanley et al. .

OTHER PUBLICATIONS

Millan et al, Chemical Abstracts, vol. 124, abstract No. 194761, 1995.
Kihara et al, Chemical Abstracts, vol. 106, abstracts No. 537, 1986.
Werner et al, Derwent Drug File Abstracts, vol. 83, abstract No. 09010, 1982.
Navarro, et al., "Efecto Sinérgico de la Meperidina y el Propranolol en el Perro," *Veterinaria Méx* 13:183–187 (1982).
STN International, File CAPlus, Accession No. 1983:432787, abstract No. 99:32787, Navarro, et al., "Synergistic Effect of Meperidine and Propranolol in Dogs," *Veterinaria Méx*. 13:183–187 (1982).
International Search Report for Swedish appl. No. 9503476–5 (priority appl. of PCT/SE96/01248), 1997.

*Primary Examiner*—William R. A. Jarvis
*Attorney, Agent, or Firm*—Michael A. Sanzo; Vinson & Elkins L.L.P.

[57] ABSTRACT

New combination of a β-receptor blocker or a pharmaceutically acceptable salt thereof, and an opioid or a pharmaceutically acceptable salt thereof, optionally in the presence of a pharmaceutically acceptable carrier or any additional agents which may be active or inactive. The new combination confers a synergistic effect, and provides unexpected efficacy in the treatment of pain.

24 Claims, No Drawings

COMBINATION OF A β-RECEPTOR BLOCKER AND AN OPIOID

This application is a 371 of PCT/SE96/01248, filed Oct. 3, 1996.

FIELD OF THE INVENTION

The present invention is related to improvements in pain relief. More specifically the invention relates to the use of a β-receptor blocker in combination with an opioid, as well as pharmaceutical compositions comprising the two active ingredients. The novel combination provides unexpected enhanced efficacy in the treatment of pain.

Background of the Invention and Prior Art

Pain is maybe the most feared and disabling consequence of illness and trauma. Pain is also the most frequent reason for patients seeking medical consultation. The human suffering has obtained significant attention among the medical community and researchers. The attention is expected to grow as the great therapeutic need is high as pain increases with the aging of a population.

Historically, opioids have been used in pain relief since the 18th century in forms for oral or injectable administration. However, the problems with opioids such as e.g. morphine, are their severe side effects which hamper their widespread use and acceptance both by physicians as well as patients. The side effects include e.g. addiction, nausea, inhibition of breathing, somnolence and dysphoria, all of which are mediated by opioid action within the brain.

Most of the side effects depend on the amount of opioid drug used. It is therefore necessary to attempt to use as low dose as possible of the opioid drug, but the problem then arises that if the dose is lowered, too much of the anaesthetic effect disappears.

In the publication by Navarro V. et al, *"Synergistic effect of meperidine and propranolol in dogs", veterinaria (Mexico City)* (1982). 13(4), 183–7, *chemical Abstracts no.* 99; 32 787, the combination of propranolol and meperidine is disclosed. However, nothing is mentioned that this combination is advantageous in the treatment of pain.

Outline of the Invention

The present invention is based on the concept of a novel combination therapy, whereby a β-receptor blocker or a pharmacologically acceptable-salt thereof, and an opioid or a physiologically and pharmaceutically acceptable salt thereof, are administered simultaneously, sequentially or in form of a pharmaceutical composition comprising the two active ingredients, optionally together with a pharmaceutically acceptable carrier.

In order to obtain the advantageous effects of the present invention, the β-receptor blocker and the opioid must be administered as a combination, either simultaneously or sequentially. In particular the dosage form and route of administration for each must be selected so that the therapeutic effects of each are manifest at the same time.

By the wording "simultaneous administration" is intended that the two active ingredients are given at the same time.

By the wording "sequential administration" is intended that the two active ingredients are given one after the other, i.e. first the β-receptor blocker is administered, and thereafter the opioid is administered or vice versa, meaning that it does not matter in which order the two active ingredients are administered. Preferably the time interval between the administration of the β-receptor blocker and the opioid, or vice versa, is not exceeding 2 hours.

Alternatively the two active ingredients may be in form of a pharmaceutical composition comprising the two active ingredients, optionally in the presence of a pharmaceutically acceptable carrier, or any additional active or inactive substances.

The β-receptor blockers which can be used for the combination therapy according to the present invention include each of the known pharmaceutically useful β-receptor blockers, e.g. alprenolol, propanolol, pindolol, sotalol, timolol and moreover selective β-receptor blockers such as metoprolol, atenolol, betaxolol, and bisoprolol. These β-receptor blockers are however only examples and should not be construed as limiting the invention in any way. Also within the scope of the invention are racemates and enantiomers of the β-receptor blockers used.

The opioids useful in the present combination similarly include any of the known therapeutically useful opioids, e.g. any of alfentanil, remifentanil, fentanyl, fenoperidin, sufentanyl, morphine and pethidine. Existing enantiomers of the opioids or active metabolites of the opioids are also within the scope of the present invention.

An advantage with the present invention is that by using the combination according to the invention in the management of pain, the side effects associated with the opioids can drasticly be reduced. By using the combination of the present invention it is possible to reduce the dose of opioids to one tenth ($1/10$) of the dose which ordinarily would provide a comparable analgesic effect.

Further, a β-receptor blocker in combination with an opioid in such low doses that under normal conditions it would not provide pain relief, offers the patient a supra-additive effect or in other words a synergistic effect in the management of pain. Surprisingly, β-receptor blockers generally have this synergistic effect in combination with opioids.

In a preferred embodiment of the invention the β-receptor blocker is metoprolol (R) and the opioid is sufentanyl.

The way of administration can be orally, rectally, intra-articularly, intrathecally, intramuscularly, intravenously, spinally, epidurally, by inhalation, nasally, bucally, sublingually or topically among others.

One preferred method of administration is topically, whereby the active ingredients are administered in form of an ointment. Topical administration is particular advantageous for the treatment of pain resulting from an inflammatory process just below the skin. Another preferred way of administration is by injection of the active ingredients intra-articularly.

Pharmaceutical Compositions

In clinical practice the active ingredients are administered simultaneously or sequentially, or alternatively in form of a pharmaceutical composition comprising the two active ingredients, either as a free base or as a pharmaceutically acceptable add addition salt, e.g. the hydrochloride, hydrobromide, lactate, acetate, sulphate, sulphamate and the like together with a pharmaceutically acceptable carrier.

The route of administration can be oral, rectal, intra-articular, intrathecal, intramuscular, intravenous, spinal, epidural, by inhalation, nasal, buccal, sublingual or topical among others.

One preferred route of administration is topical, whereby the active ingredients are administered in form of an ointment. Another preferred route of administration is by injection of the active ingredients intra-articularly.

The carrier may be a solid, semisolid or liquid diluent or capsule. These pharmaceutical compositions constitute a further aspect of this invention.

The dose of the β-receptor blocker depends on the potency, route of administration, and individual patient response. Preferably a concentration in the range 0.20–120 μmol/ml administered component is administered, more preferably in the range 0.20–100 μmol/ml administered component.

The dose of the opioid employed is substantially below that normally required to produce analgesia. Preferably a concentration in the range 0.0005–0.1 μmol/ml administered component is administered, more preferably in the range 0.001–0.08 μmol/ml administered component.

To produce pharmaceutical compositions comprising a β-receptor blocker and an opioid, in the form of dosage units for oral application, the selected compound may be mixed with a solid pulverulent carrier, e.g., lactose, saccharose, sorbitol, mannitol, starches such as potato starch, corn starch, amylopectin, laminaria powder or citrus pulp powder, cellulose derivatives, or gelatin, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g., gum arabic, gelatin, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and e.g. glycerol, the active substance may be admixed with a vegetable oil. Hard gelatin capsules may contain granules of the active substance in combination with solid, pulverulent carriers such as lactose, saccharose, sorbitol, mannitol, starches (e.g., potato starch, corn starch or amylopectin), cellulose derivatives or gelatin.

Dosage units for rectal application can be prepared in the form of suppositories comprising the active substance in admixture with a neutral fatty base, or gelatin rectal capsules comprising the active substance in admixture with vegetable oil or paraffin oil.

Detailed Description of the Invention

Biological Tests

Tests according to the tail-flick model were performed, where the sensoric and motoric effects were tested for the combinations. The purpose with these studies was to show the synergistic effect in pain management, achieved when combining a β-receptor blocker with an opioid.

Intrathecal infections in the mice were performed essentially according to Hylden and Wilcox (Hylden J L, Wilcox G L, Intrathecal morphine in mice: a new technique., Eur J Pharmacol 1980;67:313–6). A 30-G cannula was inserted between the L5 and L6 vertebrae following a small incision of the skin over this region. The different solutions were injected in a volume of 5 μl of a β-receptor blocker and 5 μl of an opioid respectively, or 5 μl of a mixture of a β-receptor blocker and an opioid.

The animals were tested for tail-flick (Åkerman B, Arweström E, Post C, Local anaesthetics potentiate spinal morphine antinociception, Anesth Analg 1988;67:943–8) reaction latencies before administration of the test compounds (pre-drug value) and 5 minutes after disappearance of the motor block. Thereafter, testing was performed every 15 minutes until the pre-drug latencies were obtained. In the tail-flick test, a thermostat-controlled light beam was directed at the tip of the tail (IITC Inc Model 33). The latency to a flick of the tail was measured and a cut-off time of 10 seconds was used. Signs of adverse effects of the test compounds were recorded. Frequency, onset and duration of motor block after intrathecal injection of 5 μl of the β-receptor blocker or 5 μl of the opioid to male mice were tested. Motor block was defined as the inability of the mouse to stand on its hind limbs and recovery was regarded as having occured when the mouse could walk and grip the floor normally.

Alprenolol racemate was used in a concentration of 1.88–15 μmol/ml, morphine was used in a concentration of 0.1–0.80 μmol/ml, fentanyl was used in a concentration of 0.01–0.80 μmol/ml, and sufentanyl was used in a concentration of 0.001–0.129 μmol/ml.

All solutions were prepared in saline 9.0 mg/ml.

The invention will now be described in more detail by way of the following Examples, which are not be construed as limiting the invention.

EXAMPLE 1

The sensoric effect of the combination of alprenolol racemate and fentanyl on tail-flick latency in mice was tested. Each concentration was tested on groups of 6 animals. The test results are shown in Table 1.

TABLE 1

| Alprenolol racemate | | Fentanyl | | Alprenolol racemate + Fentanyl | |
|---|---|---|---|---|---|
| μmol/ml | sec. | μmol/ml | sec. | μmol/ml + μmol/ml | sec. |
| 1.88 |  | 0.06 | 5.08 | 1.88 + 0.06 | 5.68 |
| 3.75 | 4.65 | 0.30 | 10.00 | 3.75 + 0.06 | 8.18 |
| 7.50 | 8.34 | 0.60 | 10.00 | 7.50 + 0.06 | 10.00 |
| 15.00 | 10.00 |  |  | 15.00 + 0.06 | 10.00 |

A solution of a concentration of alprenolol racemate single of 15 μmol/ml gave a 100% effect. In order to achieve the same effect with fentanyl single, a solution of a concentration of 0.30 μmol/ml was required. When these two substances were given in combination there was only required one half (½) of the dose of alprenolol and one fifth (⅕) the amount of the dose of fentanyl to achieve a 100% sensoric block, compared to when fentanyl was given alone. Thus, a synergistic effect is achieved in antinociceptive treatment when the β-receptor blocker is given in combination with an opioid.

EXAMPLE 2

The sensoric effect of the combination of alprenolol racemate and sufentanyl on tail-flick latency was tested on groups of 6 animals. The test results are shown in Table 2.

TABLE 2

| Alprenolol racemate | | Sufentanyl | | Alprenolol racemate + Sufentanyl | |
|---|---|---|---|---|---|
| μmol/ml | sec. | μmol/ml | sec. | μmol/ml + μmol/ml | sec. |
| 1.88 |  | 0.001 | 4.73 | 1.88 + 0.001 | 7.00 |
| 3.75 | 4.65 | 0.008 | 10.00 | 3.75 + 0.001 | 10.00 |
| 7.50 | 8.34 | 0.129 | 10.00 | 7.50 + 0.001 | 10.00 |
| 15.00 | 10.00 |  |  | 15.00 + 0.001 | 10.00 |

A solution with a concentration of 15 μmol/ml of alprenolol racemate single and 0.008 μmol/ml of sufentanyl single gave 100% sensoric block. When these two substances were given in combination, there was only required 3.75 μmol/ml of alprenolol and 0.001 μmol/ml of sufentanyl to achieve a 100% sensoric block.

This shows that the combination of alprenolol and sufentanyl confers a synergistic effect.

EXAMPLE 3

Test for Synergism

The sensoric effect of a combination of alprenolol racemate with morphine on tail-flick latency in mice was tested. Each concentration was tested on groups of 6 animals. The test results are shown in Table 3.

TABLE 3

| Alprenolol racemate | | Morphine | | Alprenolol racemate + Morphine | |
|---|---|---|---|---|---|
| μmol/ml | sec. | μmol/ml | sec. | μmol/ml + μmol/ml | sec. |
| 1.88 |  | 0.01 | 4.54 | 1.88 + 0.01 | 4.87 |
| 3.75 | 4.65 | 0.05 | 10.00 | 3.75 + 0.01 | 7.48 |
| 7.50 | 8.34 | 0.10 | 10.00 | 7.50 + 0.01 | 9.18 |
| 15.00 | 10.00 | 0.20 | 10.00 | 15.00 + 0.01 | 9.08 |

A solution with a concentration of 15 μmol/ml of alprenolol single and a solution of a concentration of 0.05 μmol/ml of morphine single gave 100% sensoric effect.

When these two substances were given in combination an amount of only 7.5 μmol/ml of alprenolol and 0.01 μmol/ml of morphine was required to achieve 95% sensoric effect. This means that there was only required an amount of morphine which was one fifth (⅕) the dose required to achieve 100% effect, compared to when morphine was given alone, and half (½) of the dose of alprenolol. Thus, a synergistic effect is achieved in antinociceptive treatment when the β-receptor blocker is given in combination with an opioid.

EXAMPLE 4

The sensoric effect of the combination of the enantiomer of Metoprolol (R) and Sufentanyl on tail-flick latency was tested on groups of 6 animals. The test results are shown in table 4.

TABLE 4

| Metoprolol (R) | | Sufentanyl | | Metoprolol (R) + Sufentanyl | |
|---|---|---|---|---|---|
| μmol/ml | sec. | μmol/ml | sec. | μmol/ml + μmol/ml | sec. |
| 60 | 5.36 | 0.001 | 5.51 | 60.0 + 0.001 | 10.00 |
| 90 | 7.64 | 0.008 | 10.00 |  |  |
| 120 | 8.58 | 0.129 | 10.00 |  |  |

A solution of a concentration of Metoprolol (R) single of 120 μmol/ml gave not a 100% effect. In order to achieve 100% effect with Sufentanyl single, a solution of a concentration of 0.008 μmol/ml was required. When these two substances were given in combination there was only required one half (½) of the dose of Metoprolol (R) and one eighth (⅛) the amount of the dose of Sufentanyl to achieve a 100% sensoric block, compared to when Metoprolol (R) or Sufentanyl are given alone. Thus, a synergistic effect is achieved in antinociceptive treatment when the β-receptor blocker is given in combination with an opioid.

Conclusion

The studies performed and described according to the present invention demonstrate that there is a synergistic effect when a β-receptor blocker is given in combination with an opioid, optionally also in the presence of a pharmaceutically acceptable carrier. The β-receptor blocker may be supplied together with an opioid, optionally also together with additional agents which may be active or inactive, in form of a kit. Agents suitable to be included in a kit will be appreciated by a person skilled in the art.

I claim:

1. A pharmaceutical composition useful in alleviating pain in a human, said composition comprising:
   (a) a β-receptor blocker or a pharmaceutically acceptable salt thereof; and
   (b) an opioid or pharmaceutically acceptable salt thereof present at a concentration of between 0.0005 and 0.1 μmol/ml.

2. The pharmaceutical composition of claim 1, wherein said β-receptor blocker is selected from the group consisting of: alprenolol and metoprolol (R).

3. The pharmaceutical composition of claim 1, wherein said opioid is selected from the group consisting of: morphine, fentanyl and sufentanyl.

4. The pharmaceutical composition of claim 1, wherein said β-receptor blocker is alprenolol and said opioid is fentanyl.

5. The pharmaceutical composition of claim 1, wherein said β-receptor blocker is alprenolol and said opioid is sufentanyl.

6. The pharmaceutical composition of claim 1, wherein said β-receptor blocker is alprenolol and said opioid is morphine.

7. The pharmaceutical composition of claim 1, wherein said β-receptor blocker is metoprolol (R) and said opioid is sufentanyl.

8. The pharmaceutical composition of claim 1, wherein said β-receptor blocker is present at a concentration of 0.20–120 μmol/ml and said opioid is present at a concentration of 0.0005–0.1 μmol/ml.

9. The pharmaceutical composition of claim 1, wherein said β-receptor blocker is present at a concentration of 0.20–100 μmol/ml and said opioid is present at a concentration of 0.001–0.08 μmol/ml.

10. The pharmaceutical composition of any one of claims 1–9, wherein said pharmaceutical composition is in a form suitable for topical administration.

11. The pharmaceutical composition of any one of claims 1–9, wherein said pharmaceutical composition is in a form suitable for administration by injection.

12. The pharmaceutical composition of any one of claims 1–9, further comprising a pharmaceutically acceptable carrier.

13. The pharmaceutical composition of claim 12, in unit dosage form.

14. A method for treating pain in a patient, comprising administering to said patient:
   (a) a β-receptor blocker, or a pharmaceutically acceptable salt thereof; and (b) an opioid, or a pharmaceutically acceptable salt thereof, wherein said β-receptor blocker and said opioid are administered simultaneously or in close enough temporal proximity so that their therapeutic effects overlap;

wherein said β-receptor blocker and said opioid are administered in a dosage sufficient to reduce or eliminate pain; and wherein said opioid is administered at a dose less than that required to obtain comparable pain relief in the absence of said β-receptor blocker.

15. The method of claim 14, wherein said β-receptor blocker is selected from the group consisting of alprenolol and metoprolol (R).

16. The method of either claim 14 or claim 15, wherein said opioid is selected from the group consisting of: morphine, fentanyl and sufentanyl.

17. The method of claim 14, wherein said β-receptor blocker is alprenolol and said opioid is fentanyl.

18. The method of claim 14, wherein said β-receptor blocker is alprenolol and said opioid is sufentanyl.

19. The method of claim 14, wherein said β-receptor blocker is alprenolol and said opioid is morphine.

20. The method of claim 14, wherein said β-receptor blocker is metoprolol (R) and said opioid is sufentanyl.

21. The method of any one of claims 14–15, or 17–20 wherein said β-receptor blocker is administered at a concentration of 0.20–1.20 μmol/ml and said opioid is administered at a concentration of 0.0005–0.1 μmol/ml.

22. The method of claim 21, wherein said β-receptor blocker is administered at a concentration of 0.20–100 μmol/ml and said opioid is administered at a concentration of 0.001–0.08 μmol/ml.

23. The pharmaceutical composition of claim 1, wherein said opioid is present at a concentration of between 0.001 and 0.08 μmol/ml.

24. The method of claim 14, wherein said opioid dose is one-tenth or less of the dose that would produce a comparable analgesic effect in the absence of said β-receptor blocker.

* * * * *